US008614352B2

(12) United States Patent
Stroefer et al.

(10) Patent No.: US 8,614,352 B2
(45) Date of Patent: Dec. 24, 2013

(54) METHOD FOR PRODUCING COLOR-STABLE MDA AND MDI

(75) Inventors: Eckhard Stroefer, Mannheim (DE); Heiner Schelling, Kirchheim (DE); Robert Reinhardt, Meckenheim (DE); Michael Zoellinger, Eislingen (DE); Daniel Breuninger, Bobenheim-Roxheim (DE); Markus Kraemer, Radeburg (DE); Kai Thiele, Antwerpen (BE); Peter Van Den Abeel, Brasschaat (BE)

(73) Assignee: BASF SE, Ludwigshafen (DE)

( * ) Notice: Subject to any disclaimer, the term of this patent is extended or adjusted under 35 U.S.C. 154(b) by 52 days.

(21) Appl. No.: 13/266,049

(22) PCT Filed: Apr. 20, 2010

(86) PCT No.: PCT/EP2010/055148
§ 371 (c)(1),
(2), (4) Date: Oct. 24, 2011

(87) PCT Pub. No.: WO2010/121997
PCT Pub. Date: Oct. 28, 2010

(65) Prior Publication Data
US 2012/0046497 A1 Feb. 23, 2012

(30) Foreign Application Priority Data
Apr. 24, 2009 (EP) .................................... 09158741

(51) Int. Cl.
C07C 211/00 (2006.01)
C09B 11/02 (2006.01)

(52) U.S. Cl.
USPC ............................ 564/333; 564/330; 564/315

(58) Field of Classification Search
None
See application file for complete search history.

(56) References Cited

U.S. PATENT DOCUMENTS

| 3,538,018 | A | 11/1970 | Pilch et al. |
| 5,053,539 | A | 10/1991 | Yano et al. |
| 5,207,942 | A | 5/1993 | Scherzer et al. |
| 5,312,971 | A | 5/1994 | Adkins et al. |
| 5,994,579 | A | 11/1999 | Torrel et al. |
| 6,031,137 | A | 2/2000 | Adkins |
| 6,140,382 | A | 10/2000 | Gallus et al. |
| 6,433,219 | B1 | 8/2002 | Strofer et al. |
| 6,639,102 | B2 | 10/2003 | Hagen et al. |
| 6,720,455 | B2 | 4/2004 | Hagen et al. |
| 6,900,348 | B1 | 5/2005 | Reif et al. |
| 6,916,953 | B2 | 7/2005 | Walsdorff et al. |
| 2001/0047112 | A1 | 11/2001 | Adkins |
| 2004/0002579 | A1 | 1/2004 | Hagen et al. |
| 2010/0217035 | A1 | 8/2010 | Knoesche et al. |
| 2011/0021836 | A1 | 1/2011 | Bock et al. |
| 2011/0028579 | A1 | 2/2011 | Zoellinger et al. |
| 2011/0124908 | A1 | 5/2011 | Rumpf et al. |
| 2011/0251425 | A1 | 10/2011 | Penzel et al. |
| 2011/0263892 | A1 | 10/2011 | Breuninger et al. |
| 2011/0319662 | A1 | 12/2011 | Olbert et al. |
| 2012/0004446 | A1 | 1/2012 | Mattke et al. |

FOREIGN PATENT DOCUMENTS

| DE | 42 08 359 | 9/1993 |
| DE | 42 32 769 | 3/1994 |
| DE | 198 15 055 | 10/1999 |
| EP | 0 445 602 | 9/1991 |
| EP | 0 451 442 | 10/1991 |
| EP | 0 962 448 | 12/1999 |
| EP | 1 270 544 | 1/2003 |
| EP | 1 288 190 | 3/2003 |
| EP | 1 344 766 | 9/2003 |
| EP | 1 375 561 | 1/2004 |
| WO | 01 00569 | 1/2001 |
| WO | 2004 014845 | 2/2004 |
| WO | 2009 013303 | 1/2009 |

OTHER PUBLICATIONS

International Search Report Issued Jun. 2, 2010 in PCT/EP10/055148 Filed Apr. 20, 2010.
U.S. Appl. No. 13/265,271, filed Oct. 19, 2011, Stroefer, et al.
U.S. Appl. No. 13/299,039, filed Nov. 17, 2011, Bock, et al.
U.S. Appl. No. 13/298,851, filed Nov. 17, 2011, Bock, et al.
U.S. Appl. No. 13/80,357, filed Dec. 22, 2011, Schelling, et al.
U.S. Appl. No. 13/383,433, filed Jan. 11, 2012, Schelling, et al.
U.S. Appl. No. 13/383,549, filed Jan. 11, 2012, Schelling, et al.
U.S. Appl. No. 13/434,135, filed Mar. 29, 2012, Lehr, et al.

Primary Examiner — Clinton Brooks
(74) Attorney, Agent, or Firm — Oblon, Spivak, McClelland, Maier & Neustadt, L.L.P.

(57) ABSTRACT

The invention relates to a process for preparing methylenediphenyldiamine (MDA) by reacting formaldehyde and aniline in the presence of an acidic catalyst, wherein the oxygen content in the process for preparing MDA is <10 000 ppm, based on all compounds present in the process.
The invention further relates to the phosgenation of MDA to methylenediphenyl diisocyanate (MDI).

20 Claims, No Drawings

METHOD FOR PRODUCING COLOR-STABLE MDA AND MDI

CROSS REFERENCE TO RELATED APPLICATIONS

The present application is a 35 U.S.C. §371 national stage patent application of International patent application PCT/EP10/055,148, filed on Apr. 20, 2010, the text of which is incorporated by reference, and claims the benefit of the filing date of European application no. 09158741.0, filed on Apr. 24, 2009, the text of each also being incorporated by reference.

The invention relates to a process for preparing methylenediphenyldiamine (MDA) by reacting formaldehyde and aniline in the presence of an acidic catalyst, wherein the oxygen content in the process is kept to a minimum. The present invention further relates to a process for preparing methylenediphenyl diisocyanate (MDI) by phosgenating MDA. The oxygen content in the MDI production too is preferably kept to a minimum.

MDA is a representative of the polyamines of the diphenylmethane series. MDA serves especially as an intermediate from which the corresponding polyisocyanate (MDI) is synthesized by phosgenation. MDI in turn is a starting material in the preparation of polyurethanes (PU), especially of polyurethane foams. A general problem with both MDA and MDI is the (inadequate) color quality. According to the preparation process used, MDA and MDI comprise various by-products which discolor the corresponding product or the polyurethanes prepared therefrom. Consequently, in the course of preparation of MDA or MDI, it should be ensured that product with very good color is prepared. Processes for preparing MDA or MDI have been known for some time.

For instance, EP-A 1 270 544 relates to a process for preparing polyisocyanates such as MDI with a hydrolyzable chlorine content of <0.1% and an iodine color number in a dilution of 1:5 in monochlorobenzene of <30, obtainable by phosgenating MDA. MDA in turn is prepared by reacting aniline with formaldehyde in the presence of acidic catalysts, wherein, in a semicontinuous process, aniline and optionally acidic catalyst are initially charged, formaldehyde and optionally acidic catalyst are fed in through a mixing unit in a circulation system in which aniline, optionally acidic catalyst, optionally formaldehyde which has already been added are circulated, and, after feeding in at least 50% of the total amount of formaldehyde to be fed in, the reaction mixture is adjusted to a temperature of >75° C.

EP-A 0 451 442 relates to a process for continuously preparing polyamines of the diphenylmethane series, wherein N-methylmethylenedianiline is present in concentrations of not greater than 0.18%. The polyamines are prepared by mixing aniline and formaldehyde with one another in the presence of hydrochloric acid in several steps and with particular molar relationships in specifically fixed temperature ranges.

The preparation of light-colored—i.e. color-stable—isocyanates such as MDI is disclosed in WO 01/00569, wherein phosgene which may contain only a maximum amount of bromine and/or iodine is used in the phosgenation. An alternative process for preparing light-colored isocyanates is described in WO 2004/014845, wherein phosgene is prepared from 2 portions of chlorine. The hydrogen chloride released in the phosgenation is converted by catalytic oxidation with oxygen to chlorine, which is in turn recycled into the process.

EP-A 1 288 190 relates to a process for preparing polyamines of the diphenylmethane series and the further reaction with phosgene to give polyisocyanates of the diphenylmethane series with a reduced color value. In this process, after the conversion of aniline and formaldehyde in the presence of an acidic catalyst, the reaction mixture is neutralized with a base at a temperature above 110° C., or the reaction mixture, after the neutralization with a base, is heated to a temperature above 110° C. An analogous process is disclosed in EP-A 1 344 766, in which, after the neutralization with the base, separation is effected into an aqueous phase and an organic phase, and the organic phase is in turn admixed with a base. According to the process described in US-A 2004/0002579, at least one alcohol is additionally present in neutralization with the base.

According to DE-A 42 08 359, color-stable isocyanates such as MDI are prepared by hydrogen treatment of the corresponding amine at a pressure of 3 to 150 bar, a temperature of 100 to 180° C. using catalysts for 15 to 4 h. In the process according to DE 198 15 055, the lightening of the color of polymeric MDI is performed by irradiating with light of wavelength from 250 to 2500 nm. According to U.S. Pat. No. 5,312,971, the phosgenation in the MDI preparation is performed in the presence of reducing agents.

EP-A 0 445 602 discloses processes for preparing MDI with a reduced iodine color number, wherein low molecular weight alkanols and/or polyhydric alcohols are added in an effective amount to the reaction mixture after the phosgenation has ended. An analogous process is disclosed in DE-A 42 32 769, according to which amines, urea compounds or mixtures thereof are added to the reaction mixture after the phosgenation has ended.

As detailed above, a wide variety of different measures are taken in the prior art in order to prepare color-stable MDA or MDI. Nowhere is it disclosed, however, that the presence of oxygen in the MDA or MDI preparation has an influence on the color stability of these two compounds.

The object underlying the present invention consists in providing an economically viable process for preparing MDA or MDI.

The object is achieved by a process for preparing methylenediphenyldiamine (MDA) by reacting formaldehyde and aniline in the presence of an acidic catalyst, wherein the oxygen content in the process for preparing MDA is <10 000 ppm, based on all compounds present in the process. Methylenediphenyl diisocyanate (MDI) can be prepared in turn from MDA by phosgenation.

The process according to the invention has the advantage that the color stability of MDA or MDI can be improved in a simple manner. Advantageously, as early as at the MDA stage, the formation of by-products is suppressed or reduced. For instance, the MDA or MDI prepared by the process according to the invention has a low proportion of coloring substances such as diarylmethane dyes (for example "Michler's hydrol blue") or triarylmethane dyes (for example "crystal violet"). The process according to the invention can prepare color-stable MDA or MDI without any need to add extraneous substances which have a positive effect on the color quality but a negative effect on the purity of the corresponding product.

The process according to the invention for preparing MDA or MDI is described in detail hereinafter.

Processes for preparing the aniline and formaldehyde reactants are known to those skilled in the art. In principle, aniline or formaldehyde can be prepared by any desired processes. Advantageously, aniline is prepared by catalytic hydrogenation of nitrobenzene in the gas phase in a fixed bed or fluidized bed. Catalysts suitable for this purpose are described, for example, in U.S. Pat. No. 3,538,018. Formaldehyde is preferably used as a solution, for example an aqueous solution. The formaldehyde solution is advantageously prepared by the silver contact process with a hydrogen excess (reducing conditions) in the reaction output of the formaldehyde synthesis. Reducing conditions are better suited than oxidizing conditions according to the Formox process with an oxygen excess in the reaction output of the formaldehyde synthesis.

The acidic catalysts used may be strong organic or strong inorganic acids. Suitable acids are, for example, hydrochloric acid (HCl), sulfuric acid, phosphoric acid or methanesulfonic acid. Preference is given to using, in the process according to the invention, aqueous hydrochloric acid, typically in concentrations of 25 to 36% by weight. Optionally, it is also possible to use gaseous HCl. In the process according to the invention, preference is given to using the acidic catalyst in aqueous form.

In the process according to the invention, the oxygen content in the preparation of MDA is <10 000 ppm (maximum oxygen value), preferably 1000 ppm, more preferably 500 ppm. The aforementioned values of the upper limit of the oxygen content in the preparation of MDA are based on all compounds present in the process. Compounds present in the process are, for example, the formaldehyde and aniline reactants, the acidic catalyst, any solvent, the MDA product, any by-products or other substances present in the process, such as additives or protective gases.

Expressed in other words, this means that, in the process according to the invention, the preparation of MDA is performed virtually or completely without oxygen. This can be achieved, for example, by minimizing the ingress of leakage air into the process and freeing one, more than one or all streams which are fed to the process or to the reaction as such of oxygen. This relates especially to the leakage gas streams in vacuum columns and/or the freeing of feed streams of oxygen dissolved therein. In this way, colored substance formation in the product can be reduced significantly.

The aforementioned maximum oxygen values in the process according to the invention are thus preferably not exceeded in the reaction vessel in which the MDA preparation is carried out, for example in a reactor. Moreover, it is preferred not to exceed the maximum oxygen values in one or more streams, especially the feed streams. This is also true of all apparatus by which the resulting product (MDA) is purified, passed or stored, for example vacuum columns, other columns, reservoir vessels, feed lines or return lines. In an advantageous manner, in the process according to the invention, the oxygen content can be reduced by degassing to a maximum oxygen value of (for example) <10 000 ppm. As already stated above, an increased oxygen content can originate from the leakage air or may already be present in dissolved form in the chemical compounds which are used in the process. The degassing to remove, for example, dissolved oxygen can be carried out by all methods known to those skilled in the art, for example by stripping, distilling, absorbing or a membrane process. The degassing is preferably effected by stripping. This is preferably carried out using one or more stripping columns. The stripping column may be present in the form of a column with random packing; a suitable stripping gas is nitrogen. In addition, the process can be carried out (or kept) under an inert gas atmosphere.

The oxygen content can, for example, be reduced by degassing in the aniline, formaldehyde or acidic catalyst feed stream used. The oxygen content can likewise also be reduced by degassing recycled streams, for example unconverted aniline by degassing. In one embodiment of the present invention, the oxygen content is reduced in the course of recycling of unconverted aniline, preferably by degassing, especially by stripping. In a further embodiment, the oxygen content in the acidic catalyst which is present in aqueous form is reduced, preferably by degassing, especially by stripping. The acidic catalyst in aqueous form is preferably hydrochloric acid.

In one embodiment, formaldehyde is provided as a formaldehyde solution in low-oxygen reduced form. In addition, aniline can be provided in low-oxygen reduced form. Preference is given to storing and holding ready the reactants or the product under inert gas, for example nitrogen or argon, especially nitrogen.

The process according to the invention can be performed in such a way that at least one of the apparatuses used in the process, especially the reaction vessel or the reactor, is operated at elevated pressure. Moreover, at least one of the apparatuses used in the process may be provided with an inert gas jacket, for example a surrounding jacket of vacuum columns comprising inert gas (jacketed columns). This jacket may be complete or partial at particularly critical sites, for example flanges.

Otherwise, MDA is prepared in the process according to the invention (for example with regard to pressure, temperature, apparatus, purifications or any additives/solvents) by methods known to those skilled in the art. In the process according to the invention, 4,4'-MDA is prepared as the main product, and 2,4'-MDA and 2,2'-MDA as by-products. For example, the process according to the invention can also be performed via the intermediate of an aminal, by first reacting formaldehyde and aniline directly and not adding the acidic catalyst until after the formation of the aminal. MDA is formed in turn from the aminal by at least double rearrangement. Such processes for preparing MDA via the aminal intermediate are known to those skilled in the art.

In addition, after the formation of MDA, a base, for example aqueous NaOH, can be added to the reaction mixture, which neutralizes or partly neutralizes the reaction mixture. The addition of base can be carried out at a temperature above 110° C.; alternatively, the temperature can be increased to a value above 110° C. only after the addition of base. In addition, the reaction mixture, after the addition of base, can be separated into an aqueous phase and an organic phase, and the organic phase can be admixed again with a base.

In one embodiment of the present invention, MDA preparation in a semicontinuous process comprises initially providing aniline and optionally acidic catalyst, feeding formaldehyde and optionally acidic catalyst through a mixing unit into a circulation system in which aniline, optionally acidic catalyst and optionally formaldehyde which has already been added are circulated, and, after feeding in at least 50% of the total amount of formaldehyde to be fed in, adjusting the reaction mixture to a temperature of >75° C.

In a further embodiment of the present invention, the MDA preparation is performed in the presence of hydrochloric acid (as the acidic catalyst) according to the following points a) to d):

a) the amount of hydrochloric acid is in the range from 0.05 to 0.5 mol per mole of aniline,
b) the amount of aniline is in the range from 1.5 to 4 mol per mole of formaldehyde,
c) the MDA preparation is divided into at least four stages, the first stage being performed at 20 to 50° C. and a water/aniline ratio in the range from 1.3 to 2.5 mol, the second stage at 40 to 70° C. and a water/aniline ratio in the range from 1.9 to 5 mol, the third stage at 50 to 90° C. and a water/aniline ratio in the range from 2.4 to 5.7 mol, and the fourth stage at a temperature of at least 110° C., and d) formaldehyde is used in at least three fractions in the stages according to point c).

In a preferred embodiment of the present invention, the MDA is converted by phosgenation to methylenediphenyl diisocyanate (MDI). Processes for preparing MDI from MDA by phosgenation are known to those skilled in the art.

In this embodiment, the process according to the invention is preferably performed in such a way that the oxygen content in the process for preparing MDI from MDA (for the MDI component step) is <10 000 ppm, based on all compounds present in the process. The oxygen content in this component step is preferably 1000 ppm, especially 500 ppm. In addition, it is preferred that the oxygen content in both component steps of the process according to the invention (MDA preparation and MDI preparation) is <10 000 ppm, based on all compounds present in the process, more preferably 1000 ppm, especially 500 ppm.

The MDA preparation and the MDI preparation can be separated from one another in terms of space and/or time. However, also conceivable is a continuous process in which freshly prepared MDA is converted further directly to MDI. This can in turn be carried out in the same reaction vessel (apparatus), but preference is given to effecting the MDA preparation and the MDI preparation in separate apparatuses which are connected to one another, for example, by lines. The reduction of the oxygen content in the MDI preparation is carried out in the process according to the invention correspondingly to the reduction of the oxygen content in the MDA preparation. For example, the oxygen content can be reduced by degassing, especially by stripping in the MDI preparation, i.e. an oxygen content of, for example, <10 000 ppm can be established.

Otherwise, the phosgenation (reaction of MDA with phosgene to give MDI) can be carried out by all methods known to those skilled in the art, for example with regard to pressure, temperature, solvent, apparatus, purification, etc. Corresponding parameters are described, for example, in EP-A 1 270 544.

In the process according to the invention, the phosgenation can be performed, for example, using a customary, preferably inert, solvent. Suitable solvents are, for example, monochlorobenzene (MCB), dichlorobenzene or other chlorinated aromatic hydrocarbons such as toluene or xylene. In the phosgenation, preferably temperatures of 70 to 120° C. and pressures of 8 to 5 bar are established. The phosgenation can be carried out in one or more stages. For example, the phosgenation can be carried out by a two-stage reaction in the presence of at least one inert organic solvent, the first stage of the phosgenation being effected in a static mixer and the second stage of the phosgenation in a delay apparatus.

According to the MDA used, in the process according to the invention, the phosgenation prepares the corresponding MDI isomers 2,2'-, 2,4'- and/or 4,4'-MDI.

In one embodiment of the present invention, the phosgene used in the phosgenation comprises less than 50 ppm of bromine or iodine or a mixture thereof. Bromine and iodine may be present in molecular or bound form.

In a further embodiment of the present invention, the phosgenation comprises the following steps a) to h):
(a) providing a first portion of chlorine, the chlorine of the first portion having a content of free or bound bromine and iodine of <400 ppm;
(b) providing a second portion of chlorine;
(c) reacting the first and second portions of chlorine with carbon monoxide to give phosgene;
(d) reacting the phosgene from step (c) with MDA to give MDI and hydrogen chloride;
(e) removing and optionally purifying the MDI formed in step (d);
(f) removing and optionally purifying the hydrogen chloride formed in step (d);
(g) catalytically oxidizing at least a portion of the hydrogen chloride removed in step (e) with oxygen to give chlorine;
(h) removing the chlorine formed in step (g) and using at least a portion of the chlorine removed as the second portion of chlorine in step (b).

The chlorine of the first portion is preferably obtained by electrolysis of a solution comprising chloride ions. It is also preferred that the chlorine of the first portion is depleted of bromine or iodine in a depletion stage. The hydrogen chloride oxidation is preferably performed under heterogeneous catalysis. Suitable catalysts for the hydrogen chloride oxidation are those comprising ruthenium oxide on a support selected from the group consisting of silicon dioxide, aluminum oxide, titanium dioxide, zirconium dioxide and mixtures thereof. The hydrogen chloride oxidation is preferably performed in a fixed bed or fluidized bed reactor.

In a further embodiment of the present invention, low molecular weight alkanols and/or polyhydric alcohols are added to the reaction mixture after the phosgenation has ended. It is optionally also possible to remove excess phosgene and the solvent and/or to treat the reaction product thermally. Suitable low molecular weight alkanols are secondary, tertiary and preferably primary alkanols with branched or preferably linear alkyl radicals with, for example, 1 to 10 carbon atoms. Examples thereof are methanol, ethanol, n- and isopropanol, n-butanol, etc. Suitable polyhydric alcohols are appropriately di- to octahydric and have a molecular weight of 60 to 350. Examples include 1,4-butanediol, triethanolpropane, glycerols or pentaerythritol.

Optionally, after removal of the excess phosgene and of the inert organic solvent and before the thermal treatment of the reaction product, at least one antioxidant based on phenol and/or at least one aryl phosphite can be added. Preferably, the antioxidant based on phenol is di-tert-butyl-p-cresol and the aryl phosphite is triphenyl phosphite. Optionally, after the phosgenation has ended, it is also possible to add amines, urea compounds or mixtures thereof.

The invention is illustrated by the examples which follow.

EXAMPLE 1

70 g of a freshly prepared polymeric methylenediphenyldiamine (MDA) are weighed under a nitrogen atmosphere into a flask with gas inlet and gas outlet and a precision glass stirrer, and heated to 50° C. with stirring. Subsequently, dry oxygen-containing nitrogen (see table 1) is allowed to flow in through the gas inlet, always with the same gas volume flows. After exactly 60 min, the gas introduction is stopped and purging is effected with pure dry nitrogen. Subsequently, the solution is diluted with 1300 ml of dry degassed monochlorobenzene (MCB) and transferred into a dropping funnel.

A reactor is initially charged with 1300 ml of MCB, and 160 g of phosgene are condensed in at room temperature. Subsequently, the solution of 1300 ml of MCB and 70 g of MDA is added dropwise from a dropping funnel to the phosgene solution at 50° C. within 60 min with stirring. Thereafter, the suspension is heated to 110° C. until it has become clear. Subsequently, the solvent is distilled off under reduced pressure up to a bottom temperature of 100° C. Subsequently, the remaining solvent is removed completely at 5 mbar and at least 60° C. The isocyanate thus obtained is transferred into a flask and treated with the aid of a rotary evaporator at 100° C. and a vacuum of 5 mbar for 45 min. Thereafter, with the same vacuum, heating is continued for 60 min until the first product distills over. After cooling, 1 g of the resulting crude MDI is dissolved in 5 g of MCB and analyzed with a Dr. Lange (LICO 500) spectral photometer. In the table below, the values obtained for the iodine color number (ICN), and the L*, a* and b* values are recorded.

TABLE 1

| $O_2$ conc. in nitrogen | CIE-LAB colors after 60 min at 180° C. | | | |
|---|---|---|---|---|
| | ICN | L* | a* | b* |
| 0 ppm | 28.0 | 74.8 | 3.4 | 58.8 |
| 50 ppm | 29.9 | 70.9 | 4.7 | 61.4 |
| 100 ppm | 32.4 | 67.2 | 6.8 | 63.8 |
| 1000 ppm | 38.6 | 61.2 | 10.3 | 68.5 |
| 5000 ppm | 44.9 | 55.8 | 11.5 | 71.5 |
| 1% | 49.6 | 50.6 | 12.4 | 73.1 |
| 21% | 61.0 | 41.0 | 17.2 | 81.3 |

According to the CIE-LAB color system, the following values are particularly advantageous for polymeric MDI:

The L* value should ideally be 100, the a* value should ideally be in the range from −10 to 0, the b* value should not be greater than 65 and the iodine color number should be at a minimum.

There is a trend clearly evident from the present data that it is advantageous when MDA is exposed to a minimum amount of oxygen. It is clearly evident from table 1 that the greatest change in the individual color values occurs in particular at the low concentrations of oxygen introduced.

It has thus been proved clearly that it is advantageous when the oxygen content in the reaction vessel or at any point in the process is <10 000 ppm, in order to obtain very good color values using the CIE-LAB color system.

The invention claimed is:

1. A process for preparing methylenediphenyldiamine (MDA) comprising reacting formaldehyde and aniline in the presence of an acidic catalyst, wherein the oxygen content in the process for preparing MDA is ≤500 ppm, based on all compounds present in the process.

2. The process according to claim 1, wherein MDA is converted by phosgenation to methylenediphenyl diisocyanate (MDI).

3. The process according to claim 2, wherein the oxygen content in the process for preparing MDI is ≤500 ppm, based on all compounds present in the process.

4. The process according to claim 1, wherein the oxygen content is reduced in the process by degassing.

5. The process according to claim 2, wherein the oxygen content is reduced in the process by degassing.

6. The process according to claim 1, wherein the oxygen content is reduced in the process by stripping, or the process is performed under an inert gas atmosphere.

7. The process according to claim 2, wherein the oxygen content is reduced in the process by stripping, or the process is performed under an inert gas atmosphere.

8. The process according to claim 1, wherein the oxygen content is reduced in the course of recycling of unconverted aniline or in the acidic catalyst which is present in aqueous form.

9. The process according to claim 2, wherein the oxygen content is reduced in the course of recycling of unconverted aniline or in the acidic catalyst which is present in aqueous form.

10. The process according to claim 1, wherein at least one of the apparatuses used in the process is provided with an inert gas jacket or is operated at elevated pressure.

11. The process according to claim 2, wherein at least one of the apparatuses used in the process is provided with an inert gas jacket or is operated at elevated pressure.

12. The process according to claim 2, wherein the phosgene used in the phosgenation comprises less than 50 ppm of bromine or iodine or a mixture thereof in molecular or bound form.

13. The process according to claim 2, wherein the phosgenation comprises the following steps a) to h):
 (a) providing a first portion of chlorine, the chlorine of the first portion having a content of free or bound bromine and iodine of <400 ppm;
 (b) providing a second portion of chlorine;
 (c) reacting the first and second portions of chlorine with carbon monoxide to give phosgene;
 (d) reacting the phosgene from step (c) with MDA to give MDI and hydrogen chloride;
 (e) removing and optionally purifying the MDI formed in step (d);
 (f) removing and optionally purifying the hydrogen chloride formed in step (d);
 (g) catalytically oxidizing at least a portion of the hydrogen chloride removed in step (e) with oxygen to give chlorine;
 (h) removing the chlorine formed in step (g) and using at least a portion of the chlorine removed as the second portion of chlorine in step (b).

14. The process according to claim 1, wherein MDA preparation in a semicontinuous process comprises initially charging aniline and optionally acidic catalyst, feeding formaldehyde and optionally acidic catalyst through a mixing unit into a circulation system in which aniline, optionally acidic catalyst and optionally formaldehyde which has already been added are circulated, and, after feeding in at least 50% of the total amount of formaldehyde to be fed in, adjusting the reaction mixture to a temperature of >75° C.

15. The process according to claim 2, wherein MDA preparation in a semicontinuous process comprises initially charging aniline and optionally acidic catalyst, feeding formaldehyde and optionally acidic catalyst through a mixing unit into a circulation system in which aniline, optionally acidic catalyst and optionally formaldehyde which has already been added are circulated, and, after feeding in at least 50% of the total amount of formaldehyde to be fed in, adjusting the reaction mixture to a temperature of >75° C.

16. The process according to claim 1, wherein the MDA preparation is performed in the presence of hydrochloric acid as the acidic catalyst according to the following points a) to d):
 a) the amount of hydrochloric acid is in the range from 0.05 to 0.5 mol per mole of aniline,
 b) the amount of aniline is in the range from 1.5 to 4 mol per mole of formaldehyde,
 c) the MDA preparation is divided into at least four stages, the first stage being performed at 20 to 50° C. and a water/aniline ratio in the range from 1.3 to 2.5 mol, the second stage at 40 to 70° C. and a water/aniline ratio in the range from 1.9 to 5 mol, the third stage at 50 to 90° C. and a water/aniline ratio in the range from 2.4 to 5.7 mol, and the fourth stage at a temperature of at least 110° C., and
 d) formaldehyde is used in at least three fractions in the stages according to point c).

17. The process according to claim 2, wherein the MDA preparation is performed in the presence of hydrochloric acid as the acidic catalyst according to the following points a) to d):

a) the amount of hydrochloric acid is in the range from 0.05 to 0.5 mol per mole of aniline,
b) the amount of aniline is in the range from 1.5 to 4 mol per mole of formaldehyde,
c) the MDA preparation is divided into at least four stages, the first stage being performed at 20 to 50° C. and a water/aniline ratio in the range from 1.3 to 2.5 mol, the second stage at 40 to 70° C. and a water/aniline ratio in the range from 1.9 to 5 mol, the third stage at 50 to 90° C. and a water/aniline ratio in the range from 2.4 to 5.7 mol, and the fourth stage at a temperature of at least 110° C., and
d) formaldehyde is used in at least three fractions in the stages according to point c).

18. The process according to claim 2, wherein low molecular weight alkanols or polyhydric alcohols are added to the reaction mixture after the phosgenation has ended.

19. The process according to claim 2, wherein low molecular weight alkanols and polyhydric alcohols are added to the reaction mixture after the phosgenation has ended.

20. The process according to claim 1, wherein the oxygen content is reduced in the course of recycling of unconverted aniline and in the acidic catalyst which is present in aqueous form.

\* \* \* \* \*